United States Patent
Cook et al.

(10) Patent No.: US 11,009,497 B2
(45) Date of Patent: May 18, 2021

(54) SYSTEMS AND METHODS FOR ESTIMATING MECHANICAL PROPERTIES OF ROCKS USING GRAIN CONTACT MODELS

(71) Applicant: BP Corporation North America Inc., Houston, TX (US)

(72) Inventors: Jennie Cook, Houston, TX (US); Abdulla Kerimov, Houston, TX (US); Nathan Lane, Katy, TX (US)

(73) Assignee: BP CORPORATION NORTH AMERICA INC., Houston, TX (US)

( * ) Notice: Subject to any disclaimer, the term of this patent is extended or adjusted under 35 U.S.C. 154(b) by 62 days.

(21) Appl. No.: 16/445,773

(22) Filed: Jun. 19, 2019

(65) Prior Publication Data

US 2019/0391125 A1 Dec. 26, 2019

Related U.S. Application Data

(60) Provisional application No. 62/688,912, filed on Jun. 22, 2018.

(51) Int. Cl.
*G06K 9/00* (2006.01)
*G01N 33/24* (2006.01)
(Continued)

(52) U.S. Cl.
CPC ........... *G01N 33/24* (2013.01); *G06T 7/0002* (2013.01); *G06T 7/11* (2017.01); *G06T 7/136* (2017.01); *G06T 2207/30181* (2013.01)

(58) Field of Classification Search
CPC .......... G01N 33/24; G06T 2207/10081; G06T 2207/30181; G06T 2207/30242;
(Continued)

(56) References Cited

U.S. PATENT DOCUMENTS

| | | |
|---|---|---|
| 6,516,080 B1 | 2/2003 | Nur |
| 8,081,796 B2 | 12/2011 | Derzhi et al. |

(Continued)

FOREIGN PATENT DOCUMENTS

| | | |
|---|---|---|
| WO | 2014142976 A1 | 9/2014 |
| WO | 2017086824 A1 | 5/2017 |
| WO | 2017086825 A1 | 5/2017 |

OTHER PUBLICATIONS

Madonna C., et al., Digital Rock Physics Numerical Prediction of Pressure-Dependent Ultrasonic Velocities using Micro-CT Imaging 2011.

(Continued)

*Primary Examiner* — Xin Jia
(74) *Attorney, Agent, or Firm* — Conley Rose, P.C.

(57) ABSTRACT

A method for analyzing a rock sample to determine a mechanical property of the rock sample includes (a) segmenting a digital image volume corresponding to an image of the rock sample. In addition, the method includes (b) partitioning the digital image volume to associate a plurality of voxels in the digital image volume with a plurality of grains of the rock sample. Further, the method includes (c) determining the voxels of the plurality of voxels that are adjacent to each other to identify a plurality of contact interfaces between the grains. Still further, the method includes (d) determining a contact area of each of the contact interfaces using adjacent voxels at the corresponding grain-grain interface. The method also includes (e) determining a number of contact interfaces that each grain of the plurality of grains has with each adjacent grain. Moreover, the method includes (f) determining the one or more mechanical properties of the rock sample based on the number of the contact interfaces of each of the plurality of grains and the contact area of each of the contact interfaces.

17 Claims, 5 Drawing Sheets

(51) Int. Cl.
  *G06T 7/136*  (2017.01)
  *G06T 7/11*  (2017.01)
  *G06T 7/00*  (2017.01)

(58) Field of Classification Search
  CPC ....... G06T 7/0002; G06T 7/0004; G06T 7/11; G06T 7/136; G06T 7/62
  See application file for complete search history.

(56) References Cited

U.S. PATENT DOCUMENTS

| | | | |
|---|---|---|---|
| 8,081,802 | B2 | 12/2011 | Dvorkin et al. |
| 8,085,974 | B2 | 12/2011 | Dvorkin et al. |
| 8,155,377 | B2 | 4/2012 | Dvorkin et al. |
| 8,170,799 | B2 | 5/2012 | Dvorkin et al. |
| 8,331,626 | B2 | 12/2012 | Wojcik et al. |
| 8,583,410 | B2 | 11/2013 | Sisk et al. |
| 8,676,556 | B2 | 3/2014 | Deffenbaugh et al. |
| 8,938,045 | B2 | 1/2015 | Dvorkin et al. |
| 9,047,513 | B2 | 6/2015 | Derzhi et al. |
| 9,070,049 | B2 | 6/2015 | Fredrich et al. |
| 9,140,117 | B2 | 9/2015 | De Prisco |
| 9,183,326 | B2 | 11/2015 | De Prisco et al. |
| 9,201,026 | B2 | 12/2015 | Walls et al. |
| 9,341,549 | B2 | 5/2016 | Lakshtanov et al. |
| 9,348,056 | B2 | 5/2016 | Fredrich et al. |
| 9,652,684 | B2 | 5/2017 | Keskes et al. |
| 9,746,431 | B2 | 8/2017 | Grader et al. |
| 2013/0262028 | A1 | 10/2013 | De Prisco et al. |
| 2015/0043787 | A1* | 2/2015 | Fredrich ............... G06T 7/136 382/109 |
| 2016/0169854 | A1 | 6/2016 | Greathouse et al. |
| 2016/0369601 | A1 | 12/2016 | Safonov et al. |
| 2016/0379356 | A1 | 12/2016 | Louis |
| 2017/0018073 | A1 | 1/2017 | Sungkorn et al. |
| 2018/0113086 | A1* | 4/2018 | Oliver ................... G01N 33/24 |

OTHER PUBLICATIONS

Saenger, E.H., et al., Towards a Representative Rock Model from a Micro-CT Image 2014.
Knackstedt, Mark A., et al., Digital Rock Physics: 3D Imaging of Core Material and Correlations to Acoustic and Flow Properties, 2009.
Arad, A., et al., Understanding Elastic Properties and Acoustic Anisotropy At the Pore/grain Scale, 2010.
Louis, L, et al., Microstructural Control on The Anisotropy of Elastic and Transport Properties in Undeformed Sandstones, 2005.
Hathon, L., et al., Controls on Acoustic Anisotropy Observed in Unconsolidated Sands Using Laboratory Measurements and Sigital Rock Technology, 2016.
Saenger, E.H., et al., Analysis of High-Resolution X-Ray Computed Tomography Images of Bentheim Sandstone Under Elevated Confining Pressures, pp. 848-859, 2016.
Øren, P.E., et al., Digital Core Laboratory: Rock and Flow Properties Derived from Computer Generated Rocks, 2006.
Knackstedt, M., et al., Rock fabric and texture from digital core analysis, 2005.
Naraghi, M.E, 3-D reconstruction of porous media and rock characterization, 2016.
Madadi, M. et al., 3D imaging and simulation of elastic properties of porous materials, 2009.
Riepe, L., et al., Application of high resolution micro-ct-imaging and pore network modeling (pnm) for the petrophysical characterization of tight gas reservoirs—a case history from a deep clastic tight gas reservoir in oman, 2011.
Zhan, X., et al., Study geophysical response of middle east carbonate reservoir using computational rock physics approach, 2012.
Kalam, M.Z., Digital rock physics for fast and accurate special core analysis in carbonates, 2012.
Derzhi, N., et al., Comparison of traditional and digital rock physics techniques to determine the elastic core parameters in thamama formation, abu dhabi, 2010.
Dvorkin, J., et al, The future of rock physics: computational methods vs. lab testing, 2008.
Li, G.G., et al., Rock physical properties computed from digital core and cuttings with applications to deep gas exploration and development, 2010.
Du,X., et al., 3-D modeling and parameters research of irregular shape particles for dem based on computerized tomography, 2011.
Wolf, K-H.A.A., et al., Mechanical behaviour of reservoir grain framework and pore characteristics: semi-quantitative predictions using microprobe combined with image analysis, 2001.
Mulchrone, K.F., et al., SAPE: a program for semi-automatic parameter extraction for strain analysis, pp. 2084-2098., 2005.
International Search Report and Written Opinion dated Sep. 18, 2019, for PCT/US2019/038094, filed on Jun. 20, 2019.
XP001575535, Mahyar Madadi and Andrew G. Christy, "A Modified coherent potential Approximation: Grain-contact moduli and coordination-number effect", Geophysics, Society of Exploration Geophysicists, vol. 77. No. 3., May 1, 2012.
XP055614160, J. Fonseca et al., "Quantitative Description of Grain Contacts in a Locked Sand", GeoX 2010, John Wiley & Sons, INc. Mar. 1, 2010.

\* cited by examiner ns and Methods for
Estimating Mechanical Properties
of Rocks Using Grain Contact
Models

CROSS-REFERENCE TO RELATED APPLICATIONS

The present application claims priority to U.S. Provisional Patent Application No. 62/688,912 filed on Jun. 22, 2018 and entitled "Systems and Methods For Estimating Mechanical Properties of Rocks Using Grain Contact Models," which is incorporated by reference herein, as if reproduced in its entirety.

BACKGROUND

In hydrocarbon production, obtaining accurate subsurface estimates of petrophysical properties of the rock formations is important for the assessment of hydrocarbon volumes contained in the rock formations and for formulating a strategy for extracting the hydrocarbons from the rock formation. Traditionally, samples of the rock formation, such as from core samples or drilling cuttings, are subjected to physical laboratory tests to measure petrophysical properties such as permeability, porosity, formation factor, elastic moduli, and the like. Some of these measurements require long time periods, extending over several months in some cases, depending on the nature of the rock itself. The equipment used to make these measurements can also be quite costly.

Due to the cost and time required to directly measure petrophysical properties, the technique of "direct numerical simulation" can be applied to efficiently estimate physical properties, such as porosity, absolute permeability, relative permeability, formation factor, elastic moduli, and the like of rock samples, including samples from difficult rock types such as tight gas sands or carbonates. According to this approach, a three-dimensional tomographic image of the rock sample is obtained, for example by way of a computer tomographic (CT) scan. Voxels in the three-dimensional image volume are "segmented" (e.g., by "thresholding" their brightness values or by another approach) to distinguish rock matrix from void space. Direct numerical simulation of fluid flow or other physical behavior such as elasticity or electrical conductivity is then performed, from which porosity, permeability (absolute and/or relative), elastic properties, electrical properties, and the like can be derived. A variety of numerical methods may be applied to solve or approximate the physical equations simulating the appropriate behavior. These methods include the Lattice-Boltzmann, finite element, finite difference, finite volume numerical methods and the like.

BRIEF SUMMARY OF THE DISCLOSURE

Embodiments of methods for analyzing a granular rock sample to determine one or more mechanical properties of the rock sample are disclosed herein. In one embodiment, the method comprises segmenting a digital image volume corresponding to an image of the rock sample. In addition, the method comprises partitioning the digital image volume to associate a plurality of voxels in the digital image volume with a plurality of grains of the rock sample. Further, the method comprises determining the voxels of the plurality of voxels that are adjacent to each other to identify a plurality of contact interfaces between the grains. Still further, the method comprises determining a contact area of each of the contact interfaces using adjacent voxels at the corresponding grain-grain interface. The method also comprises determining a number of contact interfaces that each grain of the plurality of grains has with each adjacent grain. Moreover, the method comprises determining the one or more mechanical properties of the rock sample based on the number of the contact interfaces of each of the plurality of grains and the contact area of each of the contact interfaces.

Embodiments of systems for analyzing a rock sample to determine one or more mechanical properties of the rock sample are disclosed herein. In one embodiment, the system comprises an imaging device configured to produce a digital image volume representative of the rock sample. In addition, the system comprises a computing device coupled to the imaging device. The computing device includes one or more processors and one or more storage devices coupled to the one or more processors. The one or more storage devices are configured to store instructions that, when executed by the one or more processors, configure the one or more processors to: segment a digital image volume corresponding to one or more images of the rock sample to associate voxels in the digital image volume with grains of the rock sample; partition the digital image volume to associate a plurality of voxels in the digital image volume with a plurality of grains of the rock sample; determine the voxels of the plurality of voxels that are adjacent to each other to identify a plurality of contact interfaces between the grains; determine a contact area of each of the contact interfaces using adjacent voxels at the corresponding contact interface; determine a number of contact interfaces that each grain of the plurality of grains has with each adjacent grain; and determine the one or more mechanical properties of the rock sample based on the number of the contact interfaces of each of the plurality of grains and the contact area of each of the contact interfaces.

Embodiments of non-transitory computer readable media are disclosed herein. In one embodiment, the non-transitory computer readable medium is encoded with instructions that when executed cause one or more processors to: segment a digital image volume corresponding to one or more images of the rock sample to associate voxels in the digital image volume with grains of the rock sample; partition the digital image volume to associate a plurality of voxels in the digital image volume with a plurality of grains of the rock sample; determine the voxels of the plurality of voxels that are adjacent to each other to identify a plurality of contact interfaces between the grains; determine a contact area of each of the contact interfaces using adjacent voxels at the corresponding contact interface; determine a number of contact interfaces that each grain of the plurality of grains has with each adjacent grain; and determine one or more mechanical properties of the rock sample based on the number of the contact interfaces of each of the plurality of grains and the contact area of each of the contact interfaces.

Embodiments described herein comprise a combination of features and characteristics intended to address various shortcomings associated with certain prior devices, systems, and methods. The foregoing has outlined rather broadly the features and technical characteristics of the disclosed embodiments in order that the detailed description that follows may be better understood. The various characteristics and features described above, as well as others, will be readily apparent to those skilled in the art upon reading the following detailed description, and by referring to the accompanying drawings. It should be appreciated that the conception and the specific embodiments disclosed may be readily utilized as a basis for modifying or designing other structures for carrying out the same purposes as the disclosed embodiments. It should also be realized that such equivalent constructions do not depart from the spirit and scope of the principles disclosed herein.

BRIEF DESCRIPTION OF THE DRAWINGS

For a detailed description of exemplary embodiments, reference will now be made to the accompanying drawings, which may not be drawn to scale, in which.

NOTATION AND NOMENCLATURE

Figure 1A:
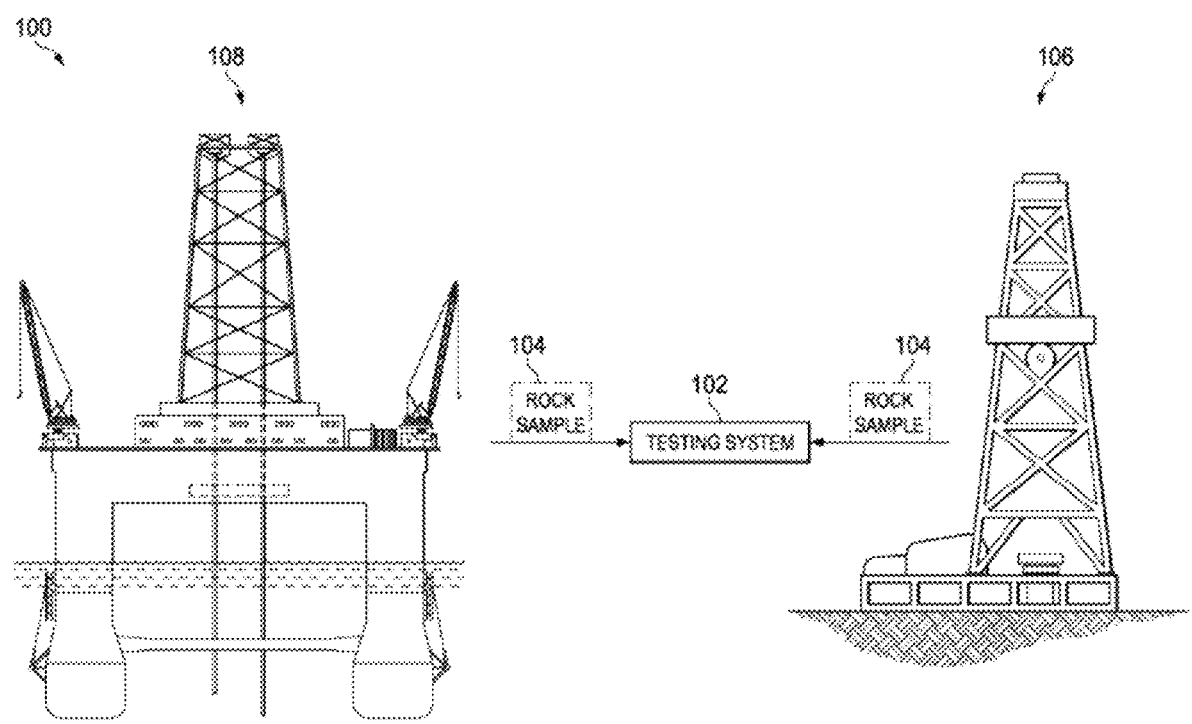
FIG. 1A is a schematic view of exemplary onshore and offshore sources of rock samples for analysis by embodiments of testing systems and methods in accordance with principles disclosed herein.

In the following discussion and in the claims, the terms "including" and "comprising" are used in an open-ended fashion, and thus should be interpreted to mean "including, but not limited to . . . ". Any use of any form of the terms "connect", "engage", "couple", "attach", or any other term describing an interaction between elements is not meant to limit the interaction to direct interaction between the elements and may also include indirect interaction between the elements described. The term "software" includes any executable code capable of running on a processor, regardless of the media used to store the software. Thus, code stored in memory (e.g., non-volatile memory), and sometimes referred to as "embedded firmware," is included within the definition of software. The recitation "based on" is intended to mean "based at least in part on." Therefore, if X is based on Y, X may be based on Y and any number of additional factors. As used herein, the terms "approximately," "about," "substantially," and the like mean within 10% (i.e., plus or minus 10%) of the recited value. Thus, for example, a recited angle of "about 80 degrees" refers to an angle ranging from 72 degrees to 88 degrees.

DETAILED DESCRIPTION

The following discussion is directed to various exemplary embodiments. However, one skilled in the art will understand that the examples disclosed herein have broad application, and that the discussion of any embodiment is meant only to be exemplary of that embodiment, and not intended to suggest that the scope of the disclosure, including the claims, is limited to that embodiment.

Certain terms are used throughout the following description and claims to refer to particular features or components. As one skilled in the art will appreciate, different persons may refer to the same feature or component by different names. This document does not intend to distinguish between components or features that differ in name but not function. The drawing figures are not necessarily to scale. Certain features and components herein may be shown exaggerated in scale or in somewhat schematic form and some details of conventional elements may not be shown in interest of clarity and conciseness.

Unless the context dictates the contrary, all ranges set forth herein should be interpreted as being inclusive of their endpoints, and open-ended ranges should be interpreted to include only commercially practical values. Similarly, all lists of values should be considered as inclusive of intermediate values unless the context indicates the contrary.

In the drawings and description that follow, like parts are typically marked throughout the specification and drawings with the same reference numerals. The drawing figures are not necessarily to scale. Certain features of embodiments may be shown exaggerated in scale or in somewhat schematic form, and some details of conventional elements may not be shown in the interest of clarity and conciseness. The present disclosure is susceptible to embodiments of different forms. Specific embodiments are described in detail and are shown in the drawings, with the understanding that the present disclosure is to be considered an exemplification of the principles of the disclosure, and is not intended to limit the disclosure to that illustrated and described herein. It is to be fully recognized that the different teachings and components of the embodiments discussed below may be employed separately or in any suitable combination to produce desired results.

In general, the bulk modulus of a substance (e.g., rock) is a measure of the ability of the substance to resist compressibility (e.g., loads oriented perpendicular to the outer surfaces of the substance), while the shear modulus of a substance (e.g., rock) describes the ability of a substance to resist shear loads (e.g., loads oriented parallel to the outer surfaces of the substance). The bulk and shear moduli of rock in a formation serve as inputs to various calculations and numerical simulations used to derive various static elastic mechanical properties of the rock including Young's modulus, Poisson's ratio, $P_{wave}$ modulus, Lame's constant, and along with material density, $P_{wave}$ velocity, and $S_{wave}$ velocity. Bulk and shear moduli of rocks are often measured in geomechanical laboratory tests. Without laboratory testing data, the bulk and shear moduli may be estimated using various rock physics models/approaches, such as Hertz-Mindlin. Such approaches require the average number of contacts between the individual grains of rock and the size (area) of those contacts as inputs to calculate the effective bulk and shear moduli of rocks. Contact number and size are estimated assuming simplified rock geometries such as spherical grains and ideal or random packing arrangements, however, these simplifications result in reduced accuracy in resulting rock property measurements.

Embodiments described herein are directed to systems and methods for determining the number and size of contacts between individual grains of rock that are used in subsequent calculations to determine the bulk and shear moduli of the rock, which in turn can be used to derive other elastic mechanical properties of the rock. In particular, embodiments described herein obtain a three-dimensional (3D) digital image volume of the rock (i.e., a digital rock), segment the 3D digital image into component grains and pore space, partition the segmented 3D digital image to identify the contacts between the component grains of rock, and then determine the number and size (area) of each of the contacts between the component grains derived from the partitioned, segmented 3D digital image. The number and size of the each of the contacts between the component grains can then be used to calculate the bulk and shear moduli of the rock.

FIG. 1A illustrates, at a high level, the acquiring of rock samples and the analysis of the rock samples according to principles disclosed herein. Embodiments of present disclosure may be especially beneficial in analyzing rock samples from sub-surface formations that are important in the production of oil and gas. As such, FIG. 1A illustrates environments 100 from which rock samples 104 to be analyzed by testing system 102 can be obtained, according to various implementations. In these illustrated examples, rock samples 104 can be obtained from terrestrial drilling system 106 or from marine (ocean, sea, lake, etc.) drilling system 108, either of which is utilized to extract resources such as hydrocarbons (oil, natural gas, etc.), water, and the like. As is fundamental in the art, optimization of oil and gas production operations is largely influenced by the structure and physical properties of the rock formations into which terrestrial drilling system 106 or marine drilling system 108 is drilling or has drilled in the past.

The manner in which rock samples 104 are obtained, and the physical form of those samples, can vary widely. Examples of rock samples 104 useful in connection with embodiments disclosed herein include whole core samples, side wall core samples, outcrop samples, drill cuttings, and laboratory generated synthetic rock samples such as sand packs and cemented packs.

As illustrated in FIG. 1A, the environment 100 includes testing system 102 that is configured to analyze images 128 (FIG. 1B) of rock samples 104 in order to determine the physical properties of the corresponding sub-surface rock, such properties including petrophysical properties in the context of oil and gas exploration and production.

Figure 1B:
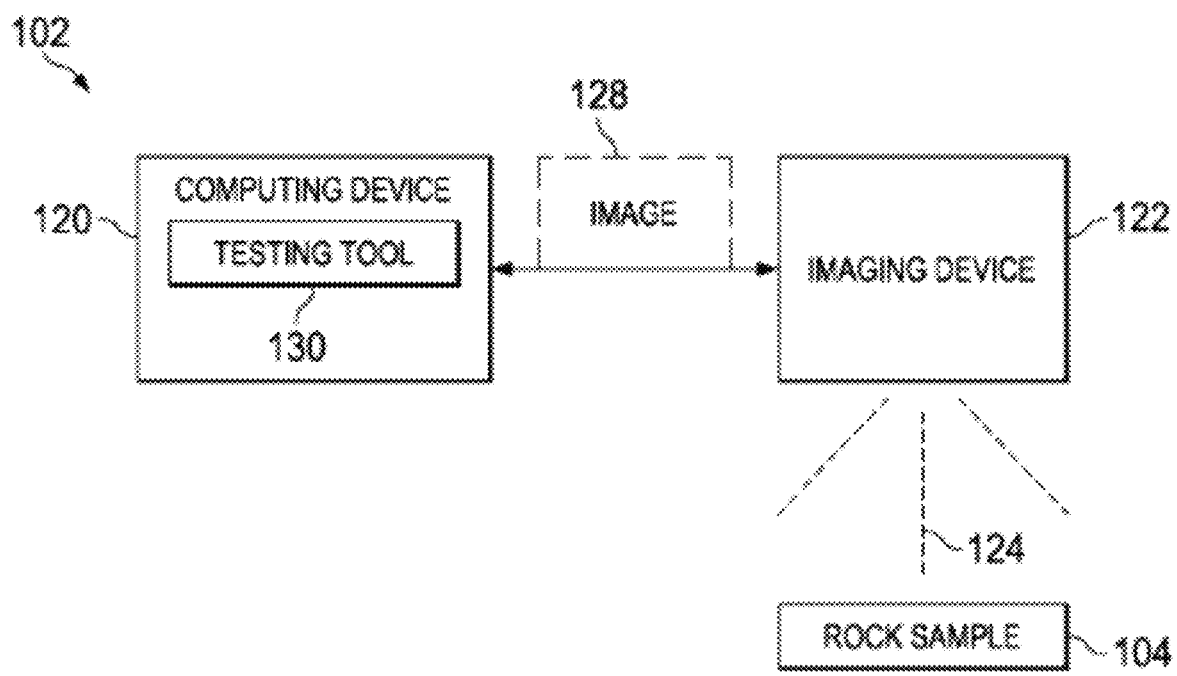
FIG. 1B is a schematic view of an embodiment of a testing system for analyzing rock samples in accordance with principles disclosed herein.

FIG. 1B illustrates, in a generic fashion, the constituent components of the testing system 102 that analyzes images 128. In a general sense, testing system 102 includes imaging device 122 for obtaining two-dimensional (2D) or three-dimensional (3D) images, as well as other representations, of rock samples 104, such images and representations including details of the internal structure of the rock samples 104. An example of imaging device 122 is an X-ray computed tomography (CT) scanner, which, as known in the art, emits x-ray radiation 124 that interacts with an object and measures the attenuation of that x-ray radiation 124 by the object in order to generate an image of its interior structure and constituents. The particular type, construction, or other attributes of CT scanner 122 can correspond to that of any type of x-ray device, such as a micro CT scanner, capable of producing an image representative of the internal structure of rock sample 104. The imaging device 122 generates one or more images 128 of rock sample 104, and forwards those images 128 to a computing device 120.

The images 128 produced by imaging device 122 may be in the form of a three-dimensional (3D) digital image volume (i.e., a digital rock) consisting of or generated from a plurality of two-dimensional (2D) sections of rock sample 104. In this case, each image volume is partitioned into 3D regular elements called volume elements, or more commonly "voxels". In general, each voxel is cubic, having a side of equal length in the x, y, and z directions. Digital image volume 128 itself, on the other hand, may contain different numbers of voxels in the x, y, and z directions. Each voxel within a digital volume has an associated numeric value, or amplitude, that represents the relative material properties of the imaged sample at that location of the medium represented by the digital volume. The range of these numeric values, commonly known as the grayscale range, depends on the type of digital volume, the granularity of the values (e.g., 8 bit or 16 bit values), and the like. For example, 16 bit data values enable the voxels of an x-ray tomographic image volume to have amplitudes ranging from 0 to 65,536 with a granularity of 1.

As mentioned above, imaging device 122 forwards images 128 to computing device 120, which in the example of FIG. 1B may be any type of computing device, for example, a desktop computer or workstation, a laptop computer, a server computer, a tablet computer, and the like. As such computing device 120 will include hardware and software components typically found in a conventional computing device. As shown in FIG. 1B, these hardware and software components of computing device 120 include a testing tool 130 that is configured to analyze images 128 to determine the petrophysical properties of rock sample 104 under one or more simulated fluid saturation conditions, including fluid saturation conditions that may be encountered by rock formations in the sub-surface. In this regard, the testing tool 130 may be implemented as software, hardware, or a combination of both, including the necessary and useful logic, instructions, routines, and algorithms for performing the functionality and processes described in further detail herein. In a general sense, testing tool 130 is configured to analyze image volume 128 of rock sample 104 to perform direct numerical simulation of the petrophysical properties under fluid saturation conditions representing subsurface conditions of rock formations, including variation degrees of saturation with multiple fluids.

Figure 1C:
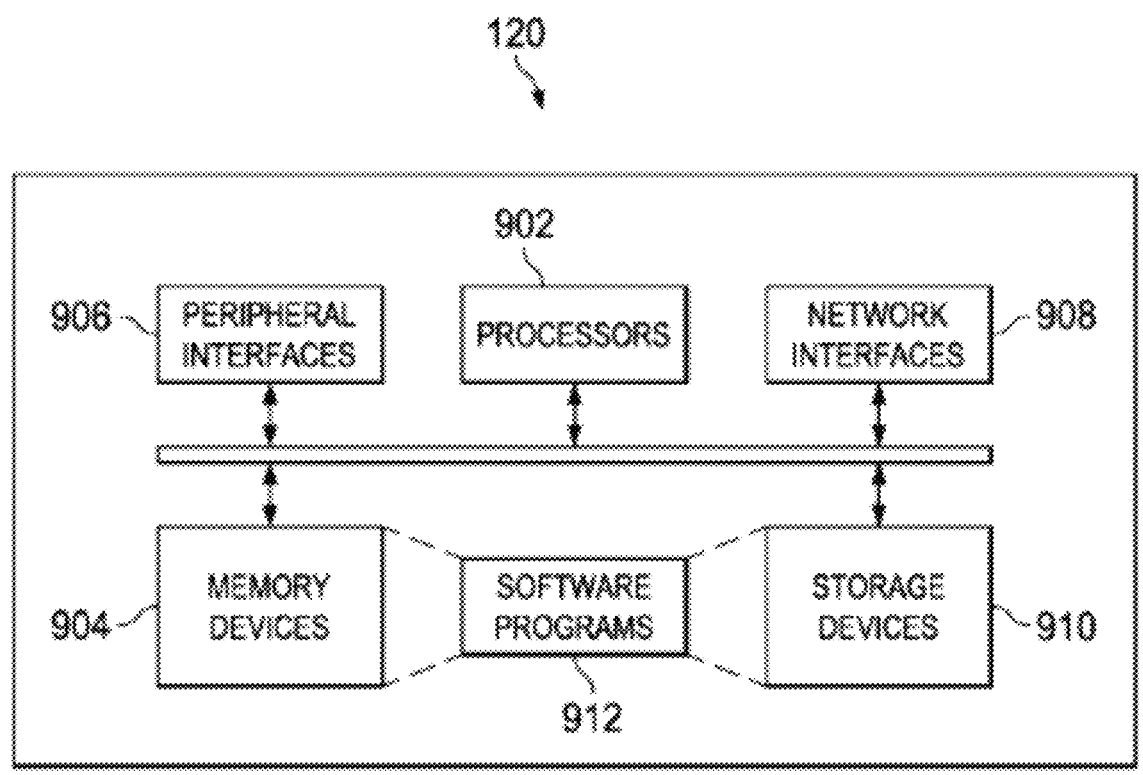
FIG. 1C is a schematic view of an embodiment of a computing device suitable for use in the testing system of FIG. 1B.

FIG. 1C generically illustrates the architecture of computing device 120 in testing system 102 according to various embodiments. In this example architecture, computing device 120 includes one or more processors 902, which may be of varying core configurations and clock frequencies as available in the industry. The memory resources of computing device 120 for storing data and/or program instructions for execution by the one or more processors 902 include one or more memory devices 904 serving as a main memory during the operation of computing device 120, and one or more storage devices 910, for example realized as one or more of non-volatile solid-state memory, magnetic or optical disk drives, or random access memory. One or more peripheral interfaces 906 are provided for coupling to corresponding peripheral devices such as displays, keyboards, mice, touchpads, touchscreens, printers, and the like. Network interfaces 908, which may be in the form of Ethernet adapters, wireless transceivers, serial network components, etc. are provided to facilitate communication between computing device 120 via one or more networks such as Ethernet, wireless Ethernet, Global System for Mobile Communications (GSM), Enhanced Data rates for GSM Evolution (EDGE), Universal Mobile Telecommunications System (UMTS), Worldwide Interoperability for Microwave Access (WiMAX), Long Term Evolution (LTE), and the like. In this example architecture, processors 902 are shown as coupled to components 904, 906, 908, and 910 by way of a single bus; of course, a different interconnection architecture such as multiple, dedicated, buses and the like may be incorporated within computing device 120.

While illustrated as a single computing device, computing device 120 can include several computing devices cooperating together to provide the functionality of a computing device. Likewise, while illustrated as a physical device, computing device 120 can also represent abstract computing devices such as virtual machines and "cloud" computing devices.

As shown in the example implementation of FIG. 1C, the computing device 120 includes software programs 912 including one or more operating systems, one or more application programs, and the like. According to embodiments, software programs 912 include program instructions corresponding to testing tool 130 (FIG. 1B), implemented as a standalone application program, as a program module that is part of another application or program, as the appropriate plug-ins or other software components for accessing testing tool software on a remote computer networked with computing device 120 via network interfaces 908, or in other forms and combinations of the same.

The program memory storing the executable instructions of software programs 912 corresponding to the functions of testing tool 130 may physically reside within computing device 120 or at other computing resources accessible to computing device 120, i.e. within the local memory resources of memory devices 904 and storage devices 910, or within a server or other network-accessible memory resources, or distributed among multiple locations. In any case, this program memory constitutes a non-transitory computer-readable medium that stores executable computer program instructions, according to which the operations described in this specification are carried out by computing device 120, or by a server or other computer coupled to computing device 120 via network interfaces 908 (e.g., in the form of an interactive application upon input data communicated from computing device 120, for display or output by peripherals coupled to computing device 120). The computer-executable software instructions corresponding to software programs 912 associated with testing tool 130 may have originally been stored on a removable or other non-volatile computer-readable storage medium (e.g., a DVD disk, flash memory, or the like), or downloadable via encoded information on an electromagnetic carrier signal, in the form of a software package from which the computer-executable software instructions were installed by computing device 120 in the conventional manner for software installation. It is contemplated that those skilled in the art will be readily able to implement the storage and retrieval of the applicable data, program instructions, and other information useful in connection with this embodiment, in a suitable manner for each particular application, without undue experimentation.

The particular computer instructions constituting software programs 912 associated with testing tool 130 may be in the form of one or more executable programs, or in the form of source code or higher-level code from which one or more executable programs are derived, assembled, interpreted or compiled. Any of a number of computer languages or protocols may be used, depending on the manner in which the desired operations are to be carried out. For example, these computer instructions for creating the model according to embodiments may be written in a conventional high level language such as PYTHON, JAVA, FORTRAN, or C++, either as a conventional linear computer program or arranged for execution in an object-oriented manner. These instructions may also be embedded within a higher-level application. In any case, it is contemplated that those skilled in the art having reference to this description will be readily able to realize, without undue experimentation, embodiments in a suitable manner for the desired installations.

The particular functions of testing tool 130, including those implemented by way of software programs 912, to analyze rock samples under various saturation conditions according to embodiments, will now be described with reference to the FIG. 2 in combination with FIGS. 1A through 1C.

Figure 2:
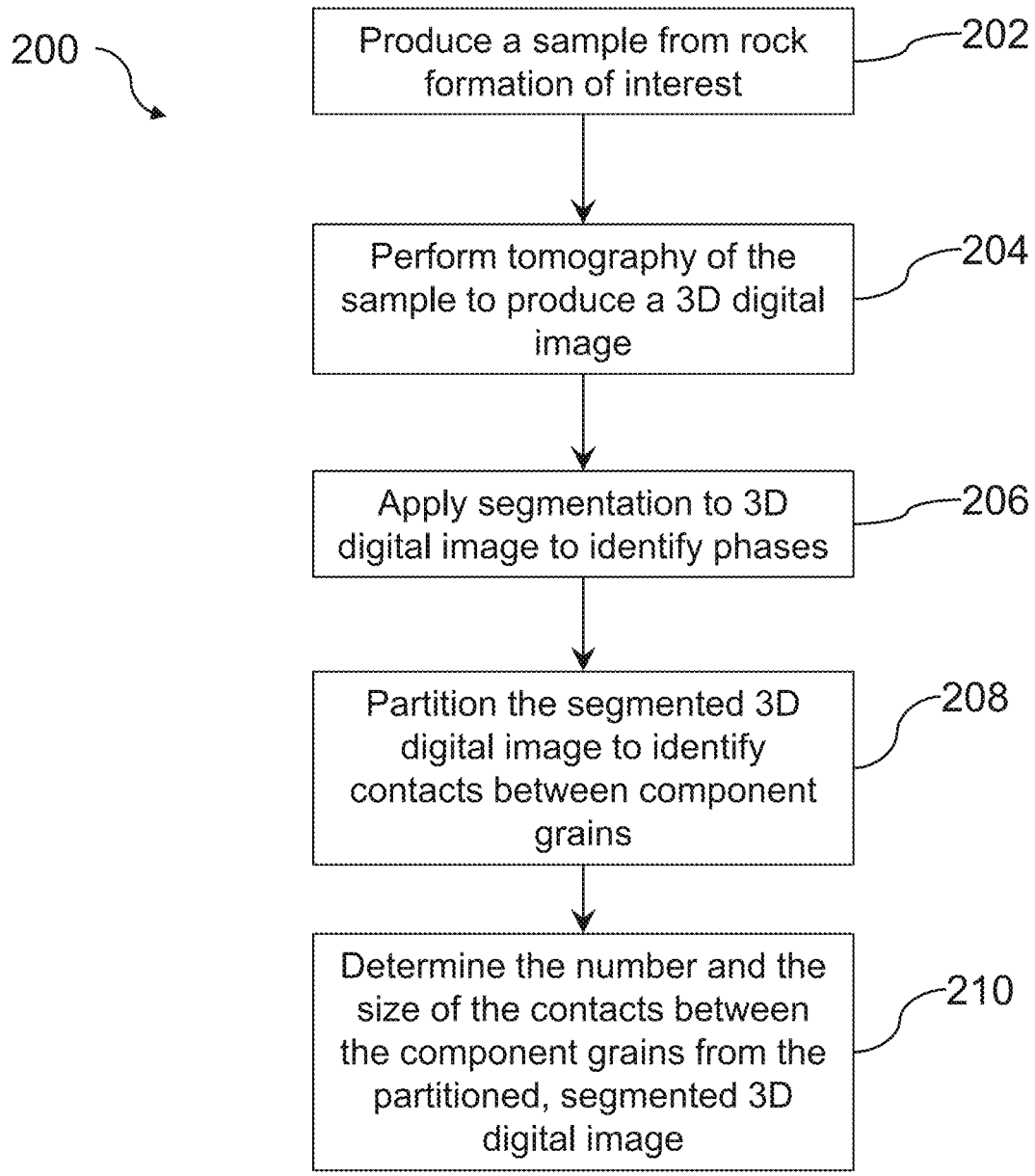
FIG. 2 is an embodiment of a method for analyzing a rock sample in accordance with principles disclosed herein.

Referring now to FIG. 2, an embodiment of a method 200 for analyzing rock samples to determine the number and size of contacts between component grains of the rock samples is shown. Though depicted sequentially as a matter of convenience, at least some of the actions shown can be performed in a different order and/or performed in parallel. Additionally, some embodiments may perform only some of the actions shown. In some embodiments, at least some of the operations of the method 200, as well as other operations described herein, can be implemented as instructions stored in a computer readable medium and executed by one or more processors 902.

In block 202, the testing system 102 acquires rock sample 104 to be analyzed, such as from a sub-surface rock formation obtained via terrestrial drilling system 106 or marine drilling system 108, or from other sources. The specific rock sample 104 may be prepared from a larger volume of the sub-surface rock formation, to be of a size, dimension, and configuration that may be imaged by imaging device 122 (e.g., a CT scanner), for example by drilling or cutting out a portion of the larger volume of the rock formation of interest.

In block 204, imaging device 122 in combination with computing device 120 of testing system 102 generates digital image volume 128 representative of rock sample 104, including its interior structure. For example, if the imaging device 122 is a CT scanner, then X-ray imaging of rock sample 104 is performed (i.e., emitting radiation directed at rock sample 104 and measuring the attenuation) to generate image volumes 128 of or from 2D slice images. Specific conventional techniques for acquiring and processing 3D digital image volumes 128 of rock sample 104 in block 204 include, without limitation, X-ray tomography, X-ray microtomography, X-ray nano-tomography, Focused Ion Beam Scanning Electron Microscopy, and Nuclear Magnetic Resonance. In some embodiments, the digital image volume 128 may be computationally generated rather than produced by scanning a physical specimen. In embodiments in which the digital image volume 128 is produced by scanning a rock specimen, the rock specimen may be a naturally occurring rock or a man-made porous material (e.g., a synthetic rock).

Figure 3A:
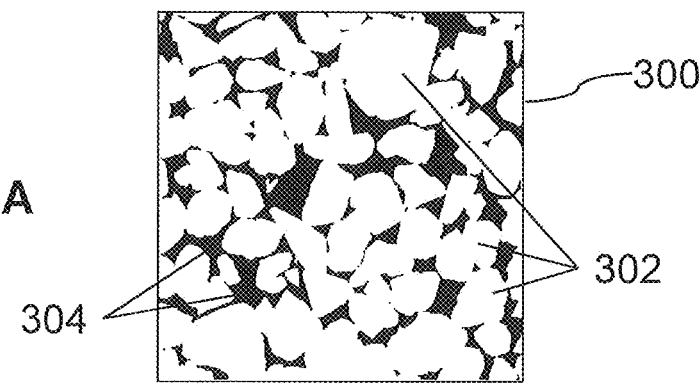
FIG. 3A is an image of a segmented two-dimensional (2D) slice of a three-dimensional (3D) image of a rock sample.

The image data at this point may be in the form of grayscale values representative of the attenuation of the x-ray radiation by the constituents of rock sample 104. As will be described momentarily, FIG. 3A illustrates an image 300 of one 2D slice through digital image volume 128, it being understood that 3D digital image volume 128 of rock sample 104 is composed of multiple 2D slice images at locations stepped along one axis of rock sample 104, which together form the 3D image of rock sample 104. In general, the combining of the 2D slice images into 3D digital image volume 128 may be performed by computational resources within imaging device 122 itself, or by computing device 120 from the series of 2D slice images 128 produced by imaging device 122, depending on the particular architecture of testing system 102.

Referring now to FIG. 3A, an example of an image 300 of one segmented 2D slice of digital image volume 128 of rock sample 104 is shown. The segmented 2D slice image 300 illustrates a cross-sectional slice of the structural details of rock sample 104, including the features of solid material 302 such as individual grains of rock (shown in white in FIG. 3A) and pore or void space 304 (shown in black in FIG. 3A). In block 206, the testing system 102 performs segmentation or other image enhancement techniques on digital image volume 128 of rock sample 104 to distinguish and label different components or phases of image volume 128 from the grayscale values of the image. The segmented digital image volume 128 may comprise a two dimensional (2D) slice image 300 that represents the rock sample 104. More specifically, computing device 120 performs this segmentation in order to identify components, such as pore space and mineralogical components (e.g., clays and quartz). In some embodiments, testing tool 130 is configured to segment image volume 128 into more than two significant phases, representing such material constituents as pore space, clay fraction, quartz fraction, and other various mineral types.

The computing device 120 can utilize any of a number of types of segmentation algorithms. One approach to segmentation is the application of a "thresholding" process to image volume 128, in which computing device 120 chooses a threshold value within the voxel amplitude range. Those voxels having an amplitude below the threshold value are assigned one specific numeric value that denotes pore space, while those voxels having an amplitude above the threshold are assigned another numeric value that denotes matrix space (i.e., solid material). In this approach, thresholding converts a grayscale image volume to a segmented volume of voxels having one of two possible numeric values, commonly selected to be 0 and 1. FIG. 3A illustrates an example of the segmentation performed on the 2D slice image 300 of 3D digital image volume 128 via thresholding. As illustrated, segmentation allows the structural details of a rock sample to be distinguished, in this example with the solid material 302 shown in different colors (various shades of gray in the grayscale image of FIG. 3A) representative of different materials in the volume 128, and pores or void space 304 shown in black. Further segmentation can be applied one or more times to differentiate various features within the image. If simple thresholding is used, multiple threshold values can distinguish among different materials exhibiting different x-ray attenuation characteristics, such as clay, quartz, feldspar, etc.

Computing device 120 may alternatively utilize other segmentation algorithms. An example of such an alternative algorithm is known in the art as Otsu's Method, in which a histogram based thresholding technique selects a threshold to minimize the combined variance of the lobes of a bimodal distribution of grayscale values (i.e., the "intra-class variance"). Otsu's method can be readily automated, and may also be extended to repeatedly threshold the image multiple times to distinguish additional material components such as quartz, clay, and feldspar. Other examples of automated segmentation algorithms of varying complexity may alternatively or additionally be used by computing device 120 to distinguish different features of an image volume, such algorithms including Indicator Kriging, Converging Active Contours, Watershedding, and the like.

The computing device 120 may also utilize other image enhancement techniques to enhance or improve the structure defined in image volume 128 to further differentiate among structure, to reduce noise effects, and the like. Likewise, while computing device 120 can perform the segmentation or other image enhancement techniques, it is contemplated that other components of testing system 102, for example imaging device 122 itself, may alternatively perform image enhancement in whole or in part.

Segmentation associates the voxels in the digital image volume with the particular material (or pore space, as the case may be) at the corresponding location within rock sample 104. Some or all of the voxels are each labeled with one or more material properties corresponding to the particular material constituent assigned to that voxel. Such constituents including pore space, matrix material, clay fraction, individual grains, grain contacts, mineral types, and the like.

Figure 3B:
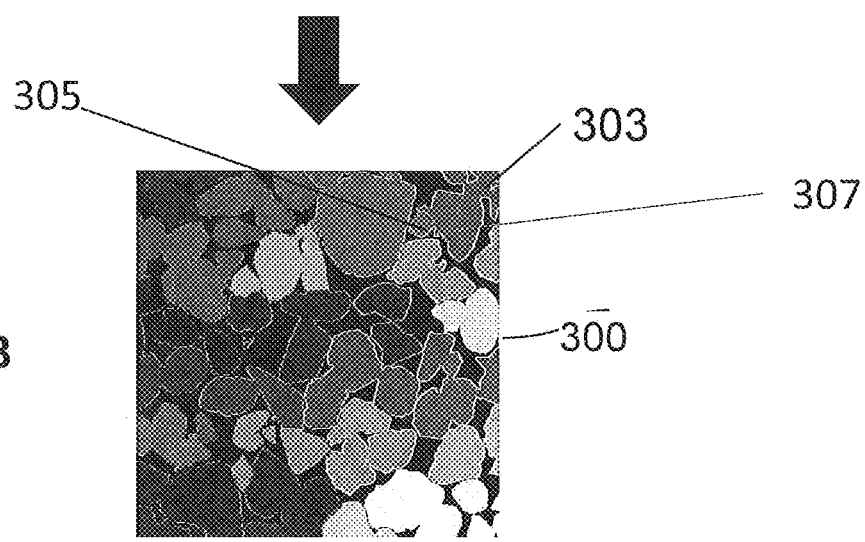
FIG. 3B is an image of the segmented two-dimensional (2D) slice of FIG. 3A after being partitioned.
Figure 3C:
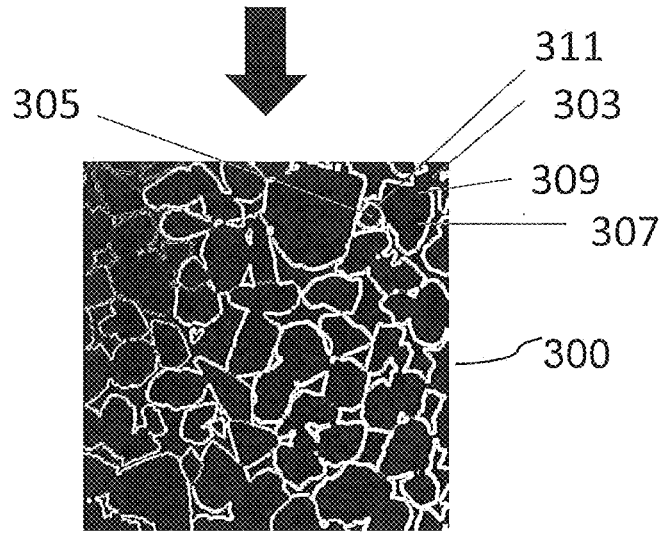
FIG. 3C is an image of the segmented and partitioned two-dimensional (2D) slice of FIG. 3B after identification of the grain contacts.

In block 208, the computing device 120 partitions the identified phases of the segmented digital image volume 128 to identify the individual contacts or contact interfaces between the component grains. The partitioning in block 208 can be performed with $3^{rd}$ party imaging software such as Avizo™ Software available from ThermoFisher Scientific™ of Hillsboro, Oreg., USA. During partitioning, each component grain may be identified in terms of voxels (e.g., voxels 303, 305, 307, as shown on FIG. 3B) in the 2D slice image 300. That is, each voxel or group of voxels define or represent a single grain, and the voxels of each grain may be represented by a different colored (or patterns, shades of grey) voxel or group of voxels as shown on FIG. 3B. FIG. 3B illustrates an example of a partitioned 2D slice image 300 of a 3D image (e.g., digital image volume 128) of a rock sample, which shows a cross-sectional slice of the structural details of that rock sample. The size (e.g., area, volume, radius (R), etc.) of each grain may be determined via imaging software. After partitioning in block 208, contacts between grains (e.g., interfaces 309, 311, as shown on FIG. 3C) are identified as an area where a voxel belonging to a grain x (e.g., voxel 303), is adjacent to a voxel belonging to a grain y (e.g., voxel 305).

In block 210, after partitioning, computing device 120 then identifies the contact interfaces between the grains (e.g., interfaces 309, 311, as shown on FIG. 3C) and then determines (e.g., calculates) the contact area (also referred to simply as "area") of each contact interface. The contact interfaces are identified by adjacent grain voxels. For example, a contact interface between two grains may be defined by a group or clump of adjacent voxels between two adjacent grains. Thus, by identifying the groups of voxels between adjacent grains, the contact interfaces between the grains can be identified. Once the contact interfaces between the grains are identified, the boundaries of the contact interfaces are known and can be used to determine (e.g., calculate) the contact area of each contact interface. The area of a contact between two voxels is the area of one of the voxel sides at the interface (e.g., a voxel is a cube). For example, if a grain x and a grain y have 100 adjacent voxels and the area of a voxel side is 4 microns$^2$, the total contact area is 400 microns$^2$.

In block 210, the contact area of each contact interface is used to determine (e.g., calculate) a contact area radius a of each contact interface. More specifically, it should be appreciated that each grain may have a unique and/or irregular 3D geometry, and as a result, the geometry or shape of the contact interface between each pair of contacting grains may be unique and/or irregular (e.g., not circular). To simplify calculations and numerical simulations (e.g., to enable use of Equations 1-4, shown below), the irregular shape of each contact interface is converted to a circle having the same contact area, and the radius a of each such circle is determined. Thus, the shape and contact area of each contact interface is effectively converted to a circle with the same area and having a radius a (also referred to as the contact area radius).

Once the contact area radius a of each contact interface is determined, the shear and normal contact stiffness of each contact interface are calculated. One method for calculating these stiffnesses are included in Equations 1 and 2 as follows:

$$S\tau = \frac{8a\mu}{2-v} \qquad \text{Equation (1)}$$

where $S\tau$ is the shear contact stiffness for the case of infinite contact friction, P is shear modulus of the grain material, v is Poisson's ratio of the grain material, and a is the contact area radius. The shear contact stiffness $S\tau$ is equal to zero for the case of zero contact friction.

$$Sn = \frac{4\mu a}{1-v} \qquad \text{Equation (2)}$$

where Sn is the normal contact stiffness; $\mu$ is shear modulus of the grain material; v is Poisson's ratio of the grain material; and a is the contact area radius.

Once shear and normal contact stiffness $S\tau$, Sn, respectively, of each contact interface is calculated with Equations 1 and 2 above, then the average shear and normal contact stiffness per grain and the average number of contacts per grain are calculated. The effective bulk and shear moduli are then calculated according to Equations 3 and 4 as follows:

$$Keff = \frac{C(1-\emptyset)}{12\pi R} Sn \qquad \text{Equation (3)}$$

where $K_{eff}$ is the effective bulk modulus, C is the number of contact interfaces per grain (also referred to as the coordination Number per grain); ø is porosity; R is grain radius; and Sn is the normal contact stiffness.

$$\mu eff = \frac{C(1-\emptyset)}{20\pi R}(Sn + 1.5S\tau) \qquad \text{Equation (4)}$$

where µeff is the effective shear modulus, C is the number of contact interfaces per grain, ø is porosity, R is grain radius, Sn is the normal contact stiffness, and $S\tau$ is the shear contact stiffness.

Figure 4:
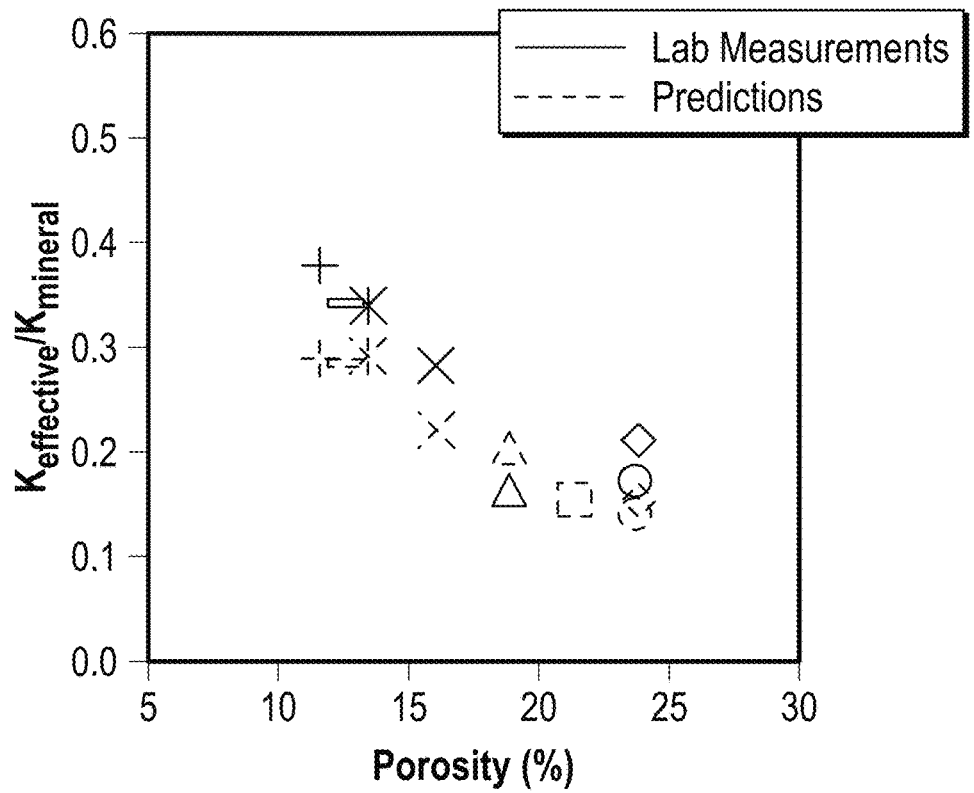
FIG. 4 is a graphical illustration of the bulk modulus of a rock sample as measured in the lab and the predicted bulk modulus of the rock sample as determined by embodiments disclosed herein (both normalized and depicted as functions of porosity)
Figure 5:
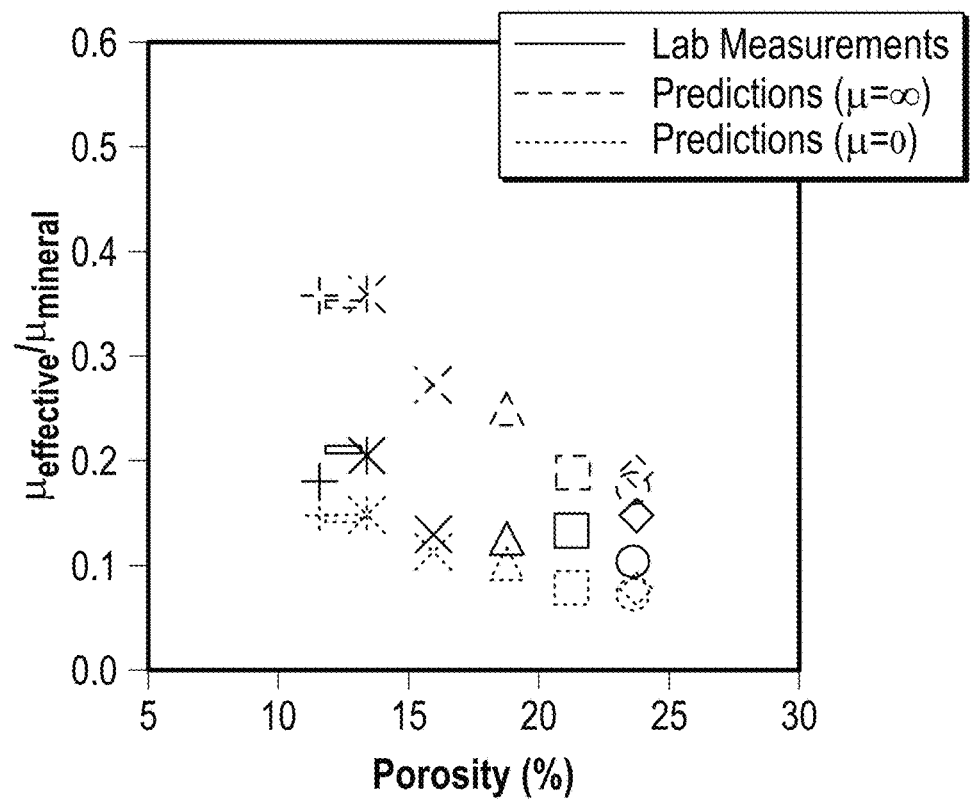
FIG. 5 is a graphical illustration of the shear modulus of a rock sample as measured in the lab and the predicted shear modulus for the rock sample as determined by embodiments disclosed herein (both normalized and depicted as functions of porosity).

The bulk and shear moduli determined using the methods and equations above can be used to derive a variety of mechanical properties of the grains and rock such as Young's modulus, Lame's constant, Poisson's ratio, $P_{wave}$ modulus, $P_{wave}$ velocity, and $S_{wave}$ velocity using techniques known in the art. It should be appreciated that distributions, minimums, maximums, and averages of the properties determined above (e.g., number of contact interfaces per grain, contact area of each contact interface, shear contact stiffness, normal contact stiffness, bulk modulus, shear modulus, etc.) across all the grains can be determined and used in subsequent calculations to determine properties across all the grains, which is representative of the properties of the rock as a whole. As compared to simplified rock property models, embodiments described herein offer the potential for improved accuracy for calculating such properties in connection with granular materials. Embodiments described herein offer the potential for enhanced delivery speed while maintaining generally acceptable accuracy. For example, FIG. 4 illustrates the bulk modulus of a rock sample as measured in the lab ("Lab measurements") as compared to the bulk modulus ($K_{effective}$) of the same rock sample as determined using embodiments of techniques disclosed herein ("Predictions"). The bulk modulus as measured in the lab and the calculated bulk modulus are both normalized by the mineral modulus ($K_{mineral}$), which is known in the art as the bulk modulus of the grain material, such as quartz, and shown in FIG. 4 as functions of porosity. As another example, FIG. 5 illustrates the shear modulus ($\mu_{effective}$) of a rock sample as measured in the lab ("Lab measurements") as compared to the shear modulus of the same rock sample as determined using embodiments of techniques disclosed herein (predicted) for the case of zero friction ("Predictions p=0") and infinite friction ("Predictions µ=∞"). The shear modulus as measured in the lab and the calculated shear moduli are normalized by the shear modulus of the grain material ($\mu_{mineral}$), which is known in the art as the shear modulus of the grain material, and shown in FIG. 5 as functions of porosity. As shown in FIG. 5, the shear modulus measured in the lab generally lays between the predicted shear moduli for the zero and infinite friction cases.

While preferred embodiments have been shown and described, modifications thereof can be made by one skilled in the art without departing from the scope or teachings herein. The embodiments described herein are exemplary only and are not limiting. Many variations and modifications of the systems, apparatus, and processes described herein are possible and are within the scope of the disclosure. For example, the relative dimensions of various parts, the materials from which the various parts are made, and other parameters can be varied. Accordingly, the scope of protection is not limited to the embodiments described herein, but is only limited by the claims that follow, the scope of which shall include all equivalents of the subject matter of the claims. Unless expressly stated otherwise, the steps in a method claim may be performed in any order. The recitation of identifiers such as (a), (b), (c) or (1), (2), (3) before steps in a method claim are not intended to and do not specify a particular order to the steps, but rather are used to simplify subsequent reference to such steps.

What is claimed is:

1. A method for analyzing a rock sample to determine one or more mechanical properties of the rock sample, the method comprising:
   (a) segmenting a digital image volume corresponding to an image of the rock sample;
   (b) partitioning the digital image volume to associate a plurality of voxels in the digital image volume with a plurality of grains of the rock sample;
   (c) determining the voxels of the plurality of voxels that are adjacent to each other to identify a plurality of contact interfaces between the grains;
   (d) determining a contact area of each of the contact interfaces using adjacent voxels at the corresponding grain-grain interface;
   (e) determining for each contact interface, a radius of a circle having an area equal to the contact area of the corresponding contact interface;
   (f) determining a number of contact interfaces that each grain of the plurality of grains has with each adjacent grain; and (g) determining the one or more mechanical properties of the rock sample based on the number of the contact interfaces of each of the plurality of grains and the radius of the circle corresponding to each of the contact interfaces.

2. The method of claim 1, wherein at least some of the plurality of contact interfaces are non-circular contact interfaces, and wherein (d) comprises determining the contact area of each of the non-circular contact interfaces using the adjacent voxels at the corresponding non-circular contact interface.

3. The method of claim 1, wherein (f) comprises determining a bulk modulus and a shear modulus of the rock sample.

4. The method of claim 1, wherein (f) comprises determining one or more of the following mechanical properties of the rock sample: a bulk modulus, a shear modulus, a Young's modulus, a Poisson's ratio, a $P_{wave}$ modulus, a $P_{wave}$ velocity, and an $S_{wave}$ velocity.

5. The method of claim 1, further comprising calculating a shear contact stiffness of the rock sample using the radius of the circle corresponding to each contact interface.

6. The method of claim 1, further comprising calculating a normal contact stiffness of the rock sample using the radius of the circle corresponding to each contact interface.

7. A system for analyzing a rock sample to determine one or more mechanical properties of the rock sample, the system comprising:
   an imaging device configured to produce a digital image volume representative of the rock sample; and
   a computing device coupled to the imaging device and comprising:
   one or more processors; and
   one or more storage devices, coupled to the one or more processors, and configured to store instructions that when executed by the one or more processors, configure the one or more processors to:
      segment a digital image volume corresponding to one or more images of the rock sample to associate voxels in the digital image volume with grains of the rock sample;
      partition the digital volume to associate a plurality of voxels in the digital image volume with a plurality of grains of the rock sample;
      determine the voxels of the plurality of voxels that are adjacent to each other to identify a plurality it of contact interfaces between the grains:
      determine a contact area of each of the contact interfaces using adjacent voxels at the corresponding contact interface;
      determine, for each contact interface, a radius of a circle having an area equal to the contact area of the corresponding contact interface;
      determine a number of contact interfaces that each grain of the plurality grains has with each adjacent grain; and
      determine the one or more mechanical properties of the rock sample based on the number of the contact interfaces of each of the plurality of grains and the radius of the circle corresponding to each of the contact interfaces.

8. The system of claim 7, wherein at least some of the plurality of contact interfaces are non-circular contact interfaces, and wherein the instructions further configure the one or more processors to: determine the contact area of each of the non-circular contact interfaces using the adjacent voxels at the corresponding non-circular contact interface.

9. The system of claim 8, wherein the one or more mechanical properties comprise a bulk modulus, a shear modulus, a Young's modulus, a Poisson's ratio, a $P_{wave}$ modulus, a $P_{wave}$ velocity, or an $S_{wave}$ velocity.

10. The system of claim 8, wherein the instructions further configure the one or more processors to, calculate a shear contact stiffness of the rock sample using the radius of the circle corresponding to each contact interface.

11. The system of claim 8, wherein the instructions further configure the one or more processors to calculate a normal contact stiffness of the rock sample using the radius of the circle corresponding to each contact interface.

12. A non-transitory computer readable medium encoded with instructions that when executed cause one or more processors to:
   segment a digital image volume corresponding to one or more of the rock sample to associate voxels in the digital image volume with grains of the rock sample;
   partition the digital image volume to associate a plurality of voxels in the digital image volume with a plurality of the rock sample;
   determine the voxels of the plurality of voxels that are adjacent to each other to identify a plurality of contact interfaces between the grains;
   determine a contact area of each of the contact interfaces using in adjacent voxels at the corresponding, contact interface;
   determine a number of contact interfaces that each grain of the plurality of grains has with each adjacent grain;
   determine, for each contact interface, a radius of a circle having an area equal to the contact area of the corresponding contact interface; and
   determine the one or more mechanical properties of the rock sample based on the number of the contact interfaces of each of the plurality of grains and the radius of the circle corresponding to each of the contact interfaces.

13. The computer readable medium of claim 12, wherein at least some of the plurality of contact interfaces are non-circular contact interfaces, and wherein the instructions further configure the one or more processors to: determine the contact area of each of the non-circular contact interfaces using the adjacent voxels at the corresponding non-circular contact interface.

14. The computer readable medium of claim 13, wherein the one or more mechanical properties comprise a bulk modulus, a shear modulus, a Young's modulus, a Poisson's ratio, a $P_{wave}$ modulus, a $P_{wave}$ velocity, or an $S_{wave}$ velocity.

15. The computer readable medium of claim 13, wherein the instructions further configure the one or more processors to, calculate a shear contact stiffness of the rock sample using the radius of the circle corresponding to each contact interface.

16. The computer readable medium of claim 13, wherein the instructions further configure the one or more processors to calculate a normal contact stiffness of the rock sample using the radius of the circle corresponding to each contact interface.

17. The computer readable medium of claim 13, wherein the one or more mechanical properties comprise a Lame's Constant.

* * * * *